(12) United States Patent
Woo et al.

(10) Patent No.: US 8,475,840 B2
(45) Date of Patent: *Jul. 2, 2013

(54) SUSTAINED RELEASE FORMULATION FOR ORAL ADMINISTRATION OF HMG-COA REDUCTASE INHIBITOR AND METHOD FOR THE PREPARATION THEREOF

(75) Inventors: Jong Soo Woo, Suwon-si (KR); Hong-Gi Yi, Suwon-si (KR); Moon-Hyuk Chi, Suwon-si (KR); Jae-Kuk Ryu, Suwon-si (KR); Si-Young Jung, Suwon-si (KR); Yong-Il Kim, Suwon-si (KR)

(73) Assignee: Hanmi Science Co., Ltd, Hwaseong-si (KR)

( * ) Notice: Subject to any disclaimer, the term of this patent is extended or adjusted under 35 U.S.C. 154(b) by 1798 days.

This patent is subject to a terminal disclaimer.

(21) Appl. No.: 10/599,729

(22) PCT Filed: Apr. 8, 2005

(86) PCT No.: PCT/KR2005/001021
§ 371 (c)(1),
(2), (4) Date: Oct. 6, 2006

(87) PCT Pub. No.: WO2005/097194
PCT Pub. Date: Oct. 20, 2005

(65) Prior Publication Data
US 2007/0196480 A1 Aug. 23, 2007

(30) Foreign Application Priority Data
Apr. 10, 2004 (KR) .................. 10-2004-0024734

(51) Int. Cl.
*A61K 47/00* (2006.01)
(52) U.S. Cl.
USPC ........... 424/468; 424/464; 424/469; 424/485; 514/460; 514/777; 514/782

(58) Field of Classification Search
USPC .................. 424/468, 464, 469, 485; 514/460, 514/777, 782
See application file for complete search history.

(56) References Cited

U.S. PATENT DOCUMENTS

| 5,135,757 | A  | * | 8/1992  | Baichwal et al. ............. 424/465 |
| 5,433,951 | A  | * | 7/1995  | Serajuddin et al. ........... 424/486 |
| 5,582,838 | A  |   | 12/1996 | Rork et al. |
| 5,882,682 | A  |   | 3/1999  | Rork et al. |
| 5,916,595 | A  |   | 6/1999  | Chen et al. |
| 6,524,615 | B2 | * | 2/2003  | Gutierrez-Rocca et al. .. 424/451 |
| 2002/0028240 | A1 |  | 3/2002 | Sawakda et al. |
| 2002/0044962 | A1 |  | 4/2002 | Cherukuri et al. |
| 2003/0091630 | A1 | * | 5/2003 | Louie-Helm et al. ......... 424/468 |
| 2004/0029962 | A1 |  | 2/2004 | Chen et al. |
| 2004/0081693 | A1 | * | 4/2004 | Woo et al. ..................... 424/468 |

FOREIGN PATENT DOCUMENTS

| JP | 04-234812 A | 8/1992 |
| JP | 04-243838 A | 8/1992 |
| JP | 11-505542 A | 5/1999 |
| JP | 11-508587 A | 7/1999 |
| JP | 2001-233766 A | 8/2001 |
| WO | 99/30692 A1 | 6/1999 |
| WO | 00/35425 A1 | 6/2000 |
| WO | 2004/010993 A1 | 2/2004 |

OTHER PUBLICATIONS

Mosquera et al., Int. J. Pharmaceutics, 1996, 135, 147-149.*

* cited by examiner

*Primary Examiner* — Abigail Fisher
(74) *Attorney, Agent, or Firm* — Sughrue Mion, PLLC

(57) ABSTRACT

The sustained release formulation for oral administration of an HMG-CoA reductase inhibitor of the present invention can be easily and economically prepared and is capable of maintaining a constant drug level in blood by slowly releasing the HMG-CoA reductase inhibitor at a uniform rate for 24 hrs. Accordingly, the sustained release formulation of the present invention can be effectively used for lowering blood cholesterol and triglyceride levels.

15 Claims, 3 Drawing Sheets

SUSTAINED RELEASE FORMULATION FOR ORAL ADMINISTRATION OF HMG-COA REDUCTASE INHIBITOR AND METHOD FOR THE PREPARATION THEREOF

FIELD OF THE INVENTION

The present invention relates to a sustained release formulation for oral administration of a 3-hydroxy-3-methylglutaryl coenzyme A (HMG-CoA) reductase inhibitor which comprises a solid dispersant, a sustained release composite carrier, and a gel hydration accelerator, wherein the solid dispersant comprises the HMG-CoA reductase inhibitor, a solubilizing agent, and a stabilizing agent; and a method for the preparation thereof.

BACKGROUND OF THE INVENTION

Hyperlipidemia or increased blood lipid level is a major cause for cardiovascular diseases and arteriosclerosis. Representative examples of hyperlipidemia are hypercholesterolemia, familial dysbetalipoproteinemia, diabetic dyslipidemia, nephrotic dyslipidemia and familial combined hyperlipidemia.

Several types of agents for lowering the blood lipid level have been developed to treat hyperlipidemia or hypercholesterolemia. Typically, these agents reduce the synthesis of lipoproteins or lipids in serum, or facilitate the removal of lipoproteins or lipids from serum or plasma. Among these agents, inhibitors of HMG-CoA reductase, a rate-limiting enzyme in the biosynthetic pathway of cholesterol, have been developed to lower the concentration of lipoproteins or lipids in serum. Exemplary HMG-CoA reductase inhibitors are: mevastatin (U.S. Pat. No.: 3,983,140), lovastatin also called mevinolin (U.S. Pat. No.: 4,231,938), pravastatin (U.S. Pat. Nos.: 4,346,227 and 4,410,629), lactone of pravastatin (U.S. Pat. No.: 4,448,979), velostatin and simvastatin, also referred to as synvinolin (U.S. Pat. Nos.: 4,448,784 and 4,450,171), rivastatin, fluvastatin, atorvastatin and cerivastatin.

The HMG-CoA reductase inhibitors have been widely used for treating hyperlipidemia for several decades to lower total in vivo concentration of cholesterol and LDL-cholesterol (Grundi, S. M, et al., N. Engl. J. Med. 319(1): 24-32, 25-26 and 31, 1998). The synthesis of mevalonate by the action of HMG-CoA is an early step in the biosynthetic pathway of cholesterol, and the HMG-CoA reductase inhibitor lowers total concentration of cholesterol and LDL-cholesterol in serum by inhibiting the synthesis of mevalonate (Grundi, S. M. et al., N. Engl. J. Med. 319(1): 24-32, 25-26 and 31, 1998).

However, most of such HMG-CoA reductase inhibitors are administered in the form of rapid release formulations, which causes side effects such as hepatoxicity, muscular disorder and rabdomyolysis (Garnet, W. R. et al., Am. J. Cardiol. 78: 20-25, 1996; The lovastatin pravastatin study group, Am. J. Cardiol. 71: 810-815, 1993; Duzovne, C. A. et al., Am. J. Med. 91: 25S-30S, 1991; and Mantel, G. M. et al., Am. J. Cardiol. 66: 11B-15B, 1990).

Accordingly, there has been a need to develop a sustained release formulation of the HMG-CoA reductase inhibitor to prevent or alleviate the side effects induced by the rapid release of HMG-CoA reductase inhibitor. Many studies on the sustained release formulation of HMG-CoA reductase inhibitor have suggested that most of the HMG-CoA reductase inhibitors absorbed in the body are metabolized in the liver (85% and more) while only 5% or less account for those transferred to the systemic circulation system. Thus, a bioavailability of the HMG-CoA reductase inhibitor to the systemic circulation system is poor. Also, as the HMG-CoA reductase inhibitor exerts its enzymatic activity mainly in the liver, it is important to understand the pharmacokinetics in the liver as well as its bioavailability. The rapid release formulation of HMG-CoA reductase inhibitor shows the dose-dependent nonlinear pharmacokinetics, but cannot maintain its therapeutic effect for a long time because of the prolonged clearance half-life caused by saturation (capacity-limited) phenomenon present during a hepatic metabolism. However, when administering the sustained release formulation of HMG-CoA reductase inhibitor, although the blood concentration of HMG-CoA reductase inhibitor may be lower than that of the rapid release formulation due to the hepatic metabolism, there is no occurrence of the saturation due to its low blood concentration. According to the latest studies, it has been reported that the sustained release formulation of HMG-CoA reductase inhibitor shows equal or slightly lower bioavailbility than the rapid release formulation in both acidic and lacton types. However, its drug delivering efficiency to a target site is shown to be superior to that of the rapid release formulation (John R, Amer. J. Cardio. 89: 15, 2002). Accordingly, the sustained release formulation is capable of more effectively lowering the LDL-cholesterol level in blood than the rapid release formulation (Monique P, Am. J. Drug Deliv. 1(4): 287-290, 2003).

The present inventors have therefore endeavored to solve the problems of the rapid release formulation of HMG-CoA reducatse inhibitor previously reported and developed a new sustained release formulation of HMG-CoA reductase inhibitor having an improved bioavailability with minimal side effects by keeping the amount of HMG-CoA reductase inhibitor at a constant level in blood through a slow and uniform release mechanism thereof.

SUMMARY OF THE INVENTION

Accordingly, it is an object of the present invention to provide a sustained release formulation for oral administration of an HMG-CoA reductase inhibitor for treating hyperlipidemia which is capable of slowly releasing the HMG-CoA reductase inhibitor at a uniform rate for a long time.

It is another object of the present invention to provide a method for the preparation of said formulation.

In accordance with one aspect of the present invention, there is provided a sustained release formulation for oral administration of an HMG-CoA reductase inhibitor which comprises a solid dispersant containing the HMG-CoA reductase inhibitor, a solubilizing agent and a stabilizing agent; a sustained release composite carrier; and a gel hydration accelerator.

In accordance with another aspect of the present invention, there is provided a method for preparing the sustained release formulation for oral administration of the HMG-CoA reductase inhibitor, which comprises the steps of:

(1) mixing the HMG-CoA reductase inhibitor, the solubilizing agent, and the stabilizing agent in a solvent to obtain the solid dispersant;

(2) homogeneously mixing the sustained release composite carrier and the gel hydration accelerator with the solid dispersant to form a first mixture;

(3) adding at least one pharmaceutically acceptable additive to the first mixture to form a second mixture; and (4) dry-mixing and formulating the second mixture into a solid formulation.

BRIEF DESCRIPTION OF THE DRAWINGS

The above and other objects and features of the present invention will become apparent from the following description of the invention, when taken in conjunction with the accompanying drawings which respectively show.

DETAILED DESCRIPTION OF THE INVENTION

Figure 1:
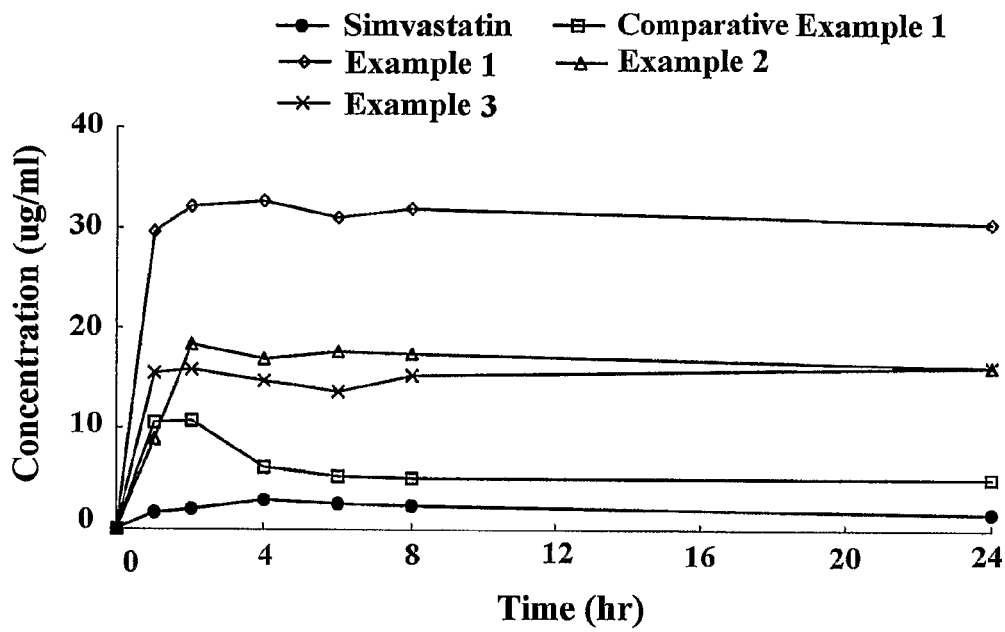
FIG. 1 shows a diagram comparing solubilities of the solid dispersants prepared in Examples 1 to 3.

The present invention provides a sustained release formulation for oral administration of an HMG-CoA reductase inhibitor which comprises a solid dispersant containing the HMG-CoA reductase inhibitor, a solubilizing agent and a stabilizing agent; a sustained release composite carrier; and a gel hydration accelerator The sustained release formulation of the present invention may be prepared by the following steps:

1) mixing the HMG-CoA reductase inhibitor, the solubilizing agent, and the stabilizing agent in a solvent to obtain the solid dispersant;

2) homogeneously mixing the sustained release composite carrier and the gel hydration accelerator with the solid dispersant to form a first mixture;

3) adding at least one pharmaceutically acceptable additive to the first mixture to form a second mixture; and 4) dry-mixing and formulating the second mixture into a solid formulation.

Since the sustained release formulation for oral administration of the present invention slowly releases the HMG-CoA reductase inhibitor into blood at a uniform rate, it is capable of maintaining a constant drug level in blood. Accordingly, the sustained release formulation for oral administration can be effectively used for preventing and treating hyperlipidemia and arteriosclerosis by orally administering once per day at a single dose.

Hereinafter, the components of the sustained release formulation of the present invention are described in detail as follows:

(i) Pharmacologically active ingredient

The HMG-CoA reductase inhibitor is a drug used for treating hyperlipidemia and arteriosclerosis by lowering lipoprotein or lipid level in blood. Representative examples thereof may include mevastatin (U.S. Pat. No.: 3,983,140), lovastatin (U.S. Pat. No.: 4,231,938), pravastatin (U.S. Pat. Nos.: 4,346,227 and 4,410,629), lactone of pravastatin (U.S. Pat. No.: 4,448,979), velostatin, simvastatin (U.S. Pat. Nos.: 4,448,784 and 4,450,171), rivastatin, fluvastatin, atorvastatin, cerivastatin, and a pharmaceutically acceptable salt thereof. Among the above-mentioned HMG-CoA reductase inhibitors, simvastatin or a pharmaceutically acceptable salt thereof is preferred.

(ii) Solubilizing agent

Since poorly water-soluble drug's bioavailability is decreased in proportion to the decrease in its solubility, the study for solubilizing the drug and increasing its solubility is essential for developing a sustained-release formulation of a poorly water-soluble drug. Since most HMG-CoA reductase inhibitors are poorly water-soluble compounds, the solubilizing agent serves to increase the drug's solubility in the present invention. Representative examples of the solubilizing agent may include vitamin E TPGS (d-α-tocopheryl polyethylene glycol 1000 succinate: Eastman), polyoxyethylene stearic acid ester (e.g., Myrj: ICI), polyethylene glycol, polyoxypropylene-polyoxypropylene block copolymer (e.g., Poloxamer: BASF) and the like. The sustained release formulation of the present invention comprises the solubilizing agent in an amount ranging from 0.05 to 20 weight part, preferably 0.1 to 10 weight part based on 1 weight part of a pharmacologically active ingredient.

(iii) Stabilizing agent

The stabilizing agent for use in the present invention may be any one of the conventional stabilizing agents, which prevents a drug from oxidizing. Exemplary stabilizing agents are butylated hydroxy toluene (BHT), butylated hydroxy anisol (BHA), erythorbic acid, ascorbic acid and the like. The inventive sustained release formulation of the present invention comprises the stabilizing agent in an amount ranging from 0.01 to 0.5 weight part, preferably 0.02 to 0.1 weight part based on 1 weight part of a pharmacologically active ingredient.

The present invention prepares the solid dispersant having an improved solubility by mixing the pharmacologically active ingredient, the solubilizing agent and the stabilizing agent according to a conventional method such as a spray-drying method, a solvent evaporating method, a finely pulverizing-wetting method, a melting method and a freeze-drying method.

In case of formulating via the spray-drying method, the solid dispersant of the present invention may further comprise a pharmaceutically acceptable solubilizing carrier. The pharmaceutically acceptable solubilizing carrier makes the solid dispersant with smaller particle sizes homogeneously distributed to improve the solubility thereof. Representative examples of the solubilizing carrier may include starch and a derivative thereof (e.g., dextrin, carboxymethyl starch); cellulose and a derivative thereof (methylcellulose, hydroxypropyl methylcellulose); saccharaids (lactose, sugar, glucose); silicic acid and silicates (natural aluminum silicic acid, magnesium silicic acid); carbonate (calcium carbonate, magnesium carbonate, sodium hydrogen carbonate); polyoxyethylene derivative; glycerin monostearate and the like.

(iv) Sustained release composite carrier

In the present invention, the sustained release composite carrier served to form a hydrogel is preferably a mixture of sodium alginate (Keltone® HVCR, Keltone® I,VF, Kelcosol® , Kelset®: ISP, USA) and xanthan gum (Keltrol® F; Kelco®, USA), and the mixture may further comprise locust bean gum (Cesagum® LN1, LR 200; Cesalpinia, Italy). Generally, the effects of the components are as follows: the sodium alginate suppresses the occurrence of an initial burst effect; the xanthan gum contributes to configuration fixation, which minimizes the difference in elution rates due to physical force such as gastrointestinal motility; and the locust bean gum can more strongly fix the configuration in combination with the xanthan gum. If the above-mentioned carrier ingredients are used in the mixture at a certain mixed ratio, the initial burst effect and the difference in elution rates due to the physical force can be reduced.

In the sustained release formulation of the present invention, the sustained release composite carrier may be used in an amount ranging from 3 to 30 weight part, preferably 5 to 25 weight part based on 1 weight part of a pharmacologically active ingredient. In case of using the mixture of sodium alginate and xanthan gum as the sustained release composite carrier, the xanthan gum is used in an amount ranging from 0.1 to 10 weight part, preferably 3 to 6 weight part based on 1 weight part of the sodium alginate. Further, in case of using the mixture of sodium alginate, xanthan gum and locust bean gum as the sustained release composite carrier, the xanthan gum is used in an amount ranging from 0.2 to 10 weight part, preferably 3 to 6 weight part, and the locust bean gum is used in an amount ranging from 0.1 to 5 weight part, preferably 0.5 to 5 weight part based on 1 weight part of the sodium alginate.

(v) Gel hydration accelerator

The gel hydration accelerator used in the present invention plays a key role in forming a single homogeneous gelated core without forming a non-gelated core. When the sustained release formulation of the present invention is brought into contact with in vivo aqueous medium, the gel hydration accelerator induces its rapid hydration and infiltrates water into an internal core of the formulation in an equal and rapid fashion. In the present invention, the gel hydration accelerator is preferably a mixture of propylene glycol ester alginate and hydroxypropyl methylcellulose (HPMC). In the above mixture, it is preferable that HPMC has a viscosity ranging from 4,000 to 100,000 cps, and the propylene glycol ester alginate is used in an amount ranging from 0.05 to 20 weight part, preferably 0.1 to 10 weight part based on 1 weight part of HPMC.

In the sustained release formulation of the present invention, the gel hydration accelerator is used in an amount ranging from 0.1 to 20 weight part, preferably, 0.5 to 15 weight part based on 1 weight part of a pharmacologically active ingredient.

Besides, the sustained release formulation of the present invention may further comprise at least one pharmaceutically acceptable additive for preparing a solid formulation for oral administration. Representative examples of the pharmaceutically acceptable additive are a binder, a lubricating agent, a sweetening agent, an excipient and the like. The binder for use in the preparation of the solid formulation may be any one of the pharmaceutically acceptable binders such as polyvinylpyrrolidone (PVP), gelatin, hydroxypropyl cellulose, kofovidone (Kollidon VA64: BASF, Germany) and the like.

The lubricating agent for use in the present invention may be any one of the pharmaceutically acceptable lubricating agents, which increases fluidity. Representative examples thereof may include light anhydrous silicic acid, zinc or magnesium salt of stearate, and the like.

Further, the present invention provides a method for preparing the sustained release formulation for oral administration of the HMG-CoA reductase inhibitor.

The method of the present invention comprises the following steps (1) mixing the HMG-CoA reductase inhibitor, the solubilizing agent, and the stabilizing agent in a solvent to obtain the solid dispersant;

(2) homogeneously mixing the sustained release composite carrier and the gel hydration accelerator with the solid dispersant to form a first mixture;

(3) adding at least one pharmaceutically acceptable additive to the first mixture to form a second mixture; and (4) dry-mixing and formulating the second mixture into a solid formulation.

Additionally, the method of the present invention may further comprise the step of coating the surface of the solid formulation prepared in step (4) with any one of the pharmaceutically acceptable coating agents. Representative examples of the coating agent may include hydroxypropyl methylcellulose, polyethylene glycol, polyvinyl alcohol and the like.

In step (1), the solid dispersant may be prepared by a conventional method such as a spray-drying method, a solvent evaporating method, a finely pulverizing-wetting method, a melting method and a freeze-drying method, and it is preferable to have a particle size ranging from 5 to 200 μm in diameter. The solvent used for dissolving the HMG-CoA reductase inhibitor, the solubilizing agent, and the stabilizing agent is preferably water, ethanol or methylene chloride.

The dried mixture obtained in step 4) may be formulated into soft and hard capsules in accordance with the conventional procedures. In a preferred embodiment of the present invention, the second mixture of step (4) may be compressed into a tablet according to a direct tablet-forming method or formulated into a tablet after compressing and pulverizing.

A typical daily dose of the sustained release formulation for oral administration of the HMG-CoA reductase inhibitor can be in the form of a single dose or in divided doses.

The following Examples are intended to further illustrate the present invention without limiting its scope.

EXAMPLES 1 to 3

Preparation of Solid Dispersants

Simvastatin (Hanmi Fine Chemical Co., Ltd., Korea), vitamin E TPGS (Eastman, USA), BHT (UENO Fine Chemical, USA) and HPMC 2910 (Shin-Etsu, Japan) were dissolved in ethanol according to the following amount as described in Table 1 (Examples 1 to 3; experimental groups), and each of the resulting mixtures was subjected to spray-drying, to obtain a sold dispersant having an average particle size of 100 μm and below. As a comparative group, the solid dispersant was prepared by mixing only simvastatin and HPMC 2910 in ethanol (Comparative Example 1).

TABLE 1

| Composition (mg/dispersant) | Simvastatin | Vitamin E TPGS | BHT | HPMC 2910 |
|---|---|---|---|---|
| Comparative Example 1 | 40 | X | X | 100 |
| Example 1 | 40 | 80 | 2 | 100 |
| Example 2 | 40 | 40 | 2 | 100 |
| Example 3 | 40 | 40 | 2 | 50 |

EXAMPLES 4 to 12

Preparation of Sustained Release Formulations for Oral Administration

Simvastatin, vitamin E TPGS, Myrj, BHT and HPMC 2910 were mixed to prepare solid dispersants according to the same method as described in Example 1

Then, each of the solid dispersants was mixed with sodium alginate (ISP, USA), xanthan gum (Kelco, USA), locust bean gum (Cesalpinia, Italy), propylene glycol ester alginate (ISP, USA), HPMC 2208 (Shin-Etsu, Japan) and kofovidone (BASF, Germany) for about 30 min. Magnesium stearate and light anhydrous silicic acid powders (finer than mesh 40) were added to the mixture, and mixed for 5 min. The resulting mixture was mold into a mass using a shaping assembler, and the mass was crushed down into particles having a mesh size ranging from 20 to 80. The particles were then formulated into a tablet by conventional compressing in a formulator. Next, the sustained release formulations for oral administration of Example 5 to 12 were prepared according to the same method as described above. The amount of each ingredient is shown in Tables 2 to 4. At this time, HPMC 2208 used in all Examples had a viscosity of 100,000 cps, and Examples 11 and 12 used lovastatin and fluvastatin as a pharmacologically active ingredient instead of using simvastatin, respectively.

TABLE 4-continued

| Component (mg/tablet) | Example 12 |
|---|---|
| BHT | 2 |
| HPMC 2910 | 60 |
| Sodium alginate | 40 |
| Xantan gum | 150 |
| Locust bean gum | 80 |
| Propylene glycol ester alginate | 35 |
| HPMC 2208 | 110 |
| Kofovidone | 35 |
| Light anhydrous silicic acid | 10 |
| Magnesium stearate | 2 |

TABLE 2

| Component (mg/tablet) | Example 4 | Example 5 | Example 6 | Example 7 | Example 8 | Example 9 | Example 10 |
|---|---|---|---|---|---|---|---|
| Simvastatin | 40 | 40 | 40 | 40 | 40 | 40 | 40 |
| Vitamin E TPGS | 40 | 40 | 40 | 40 | 40 | 40 | 0 |
| Myrj | 0 | 0 | 0 | 0 | 0 | 0 | 40 |
| BHT | 2 | 2 | 2 | 2 | 2 | 2 | 2 |
| HPMC 2910 | 50 | 50 | 50 | 50 | 50 | 50 | 50 |
| Sodium alginate | 36 | 36 | 36 | 36 | 36 | 36 | 36 |
| Xantan gum | 100 | 120 | 160 | 160 | 160 | 160 | 120 |
| Locust bean gum | 60 | 60 | 60 | 60 | 60 | 60 | 60 |
| Propylene glycol ester alginate | 36 | 36 | 36 | 36 | 36 | 36 | 36 |
| HPMC 2208 | 160 | 160 | 160 | 40 | 80 | 120 | 160 |
| Kofovidone | 35 | 35 | 35 | 35 | 35 | 35 | 35 |
| Light anhydrous silicic acid | 10 | 10 | 10 | 10 | 10 | 10 | 10 |
| Magnesium stearate | 2 | 2 | 2 | 2 | 2 | 2 | 2 |

TABLE 3

| Component (mg/tablet) | Example 11 |
|---|---|
| Lovastatin | 60 |
| Vitamin E TPGS | 20 |
| BHT | 2 |
| HPMC 2910 | 50 |
| Sodium alginate | 36 |
| Xantan gum | 150 |
| Locust bean gum | 50 |
| Propylene glycol ester alginate | 30 |
| HPMC 2208 | 110 |
| Kofovidone | 35 |
| Light anhydrous silicic acid | 10 |
| Magnesium stearate | 2 |

TABLE 4

| Component (mg/tablet) | Example 12 |
|---|---|
| Fluvastatin | 80 |
| Vitamin E TPGS | 60 |

Test Example 1

Solubility Test of Solid Dispersants

The solid dispersants of Comparative Example 1 and Examples 1 to 3, and a raw simvastatin powder as a control group were subjected to solubility test in distilled water using a dissolution-test system under the following conditions according to the 1$^{st}$ Basket method described in Korea Pharmacopoeia.

Dissolution-test system: Erweka DT 80 (Erweka, Germany)
Effluent: 900 mλ of distilled water
Temperature of effluent: 37±0.5° C.
Rotational speed: 50, 100 and 150 rpm
Analytic method: liquid chromatography
Column: Cosmosil $C_{18}$ (Nacalai tesque)
Mobile phase: acetonitrile/pH 4.0 buffer solution*
Flow rate: 1.5 mλ/min
Detector: ultraviolet spectrophotometer (238 nm)
Injection volume: 20 μλ pH 4.0 buffer solution was prepared by mixing 3 mλ of glacial acetic acid with 1 λ of distilled water and adjusting the mixture's pH to 4.0 with NaOH.

As can be seen in FIG. 1, it was found that the solid dispersants of Examples 1 to 3 prepared by spray-drying the mixture of simvastatin, vitamin E TPGS and HPMC showed higher solubilities than the solid dispersant of Comparative Example 1 prepared by mixing only simvastatin and HPMC and the raw simvastatin powder, and their solubilities were rather proportional to the amount of vitamin E TPGS than HPMC.

Test Example 2

Dissolution Test for Rotational Speed

The formulation prepared in Example 5 was subjected to in vitro dissolution test under the following conditions according to the $1^{st}$ Paddle method described in Korea Pharmacopoeia. The amount of simvastatin eluted from the formulation during the test was measured by liquid chromatography at 1, 2, 4, 6, 8, 10, 12, 16, 20 and 24 hrs after the administration. Each sample was left with 40 mg of the pre-washed $MnO_2$ (under USP Simvastatin Tablet 1) for reaction therewith for 30 min and centrifuged at 3,000 rpm for 5 min. Then, the absorbance of each sample was measured using a ultraviolet spectrophotometer and its real absorbance was calculated by subtracting the absorbance at 257 nm from that at 247 nm.

Figure 2:
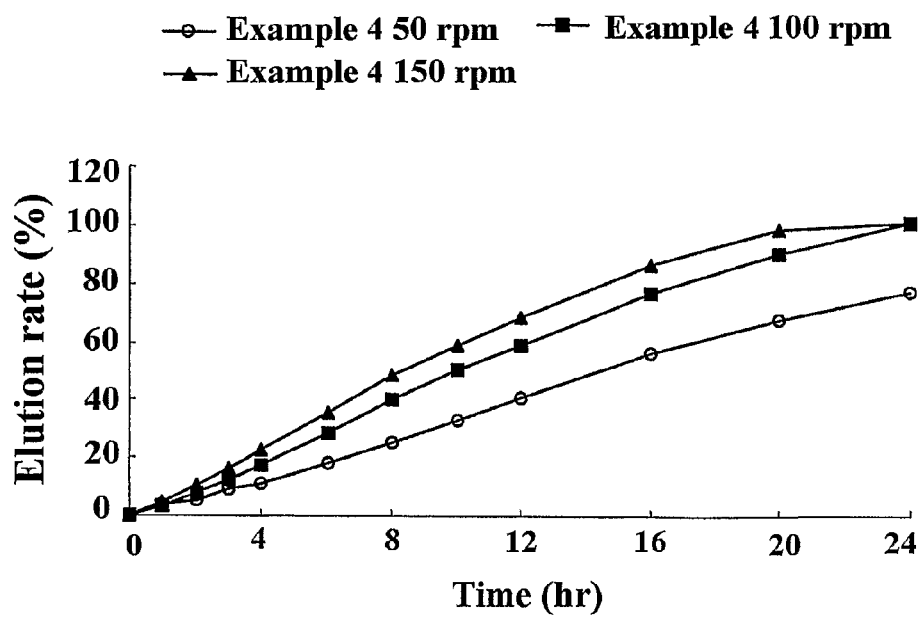
FIG. 2 illustrates graphs representing elution rates of the sustained release formulations prepared in Example 4, the graphs being shown for each rotational speed.

Dissolution-test system: Erweka DT 80
Effluent: 0.01 M sodium phosphate buffer solution (pH 7.0) containing 5% sodium lauryl sulfate (SLS)
Temperature of effluent: 37±0.5° C.
Rotational speed: 50, 100 and 150 rpm
Analytic method: ultraviolet spectrophotometer (247 nm and 257 nm)
Calculation of eluted amount: Cumulative release amount As shown in FIG. 2, it was found that the simvastatin formulation of the present invention did not show any significant difference in the dissolution rate by the change in the rotational speed, indicating that bioavailability is reproducible.

Test Example 3

Dissolution test for the amount of xanthan gum

The formulations prepared in Example 4 to 6 were subjected to in vitro dissolution test at 100 rpm according to the same method as described in Test Example 2.

Figure 3:
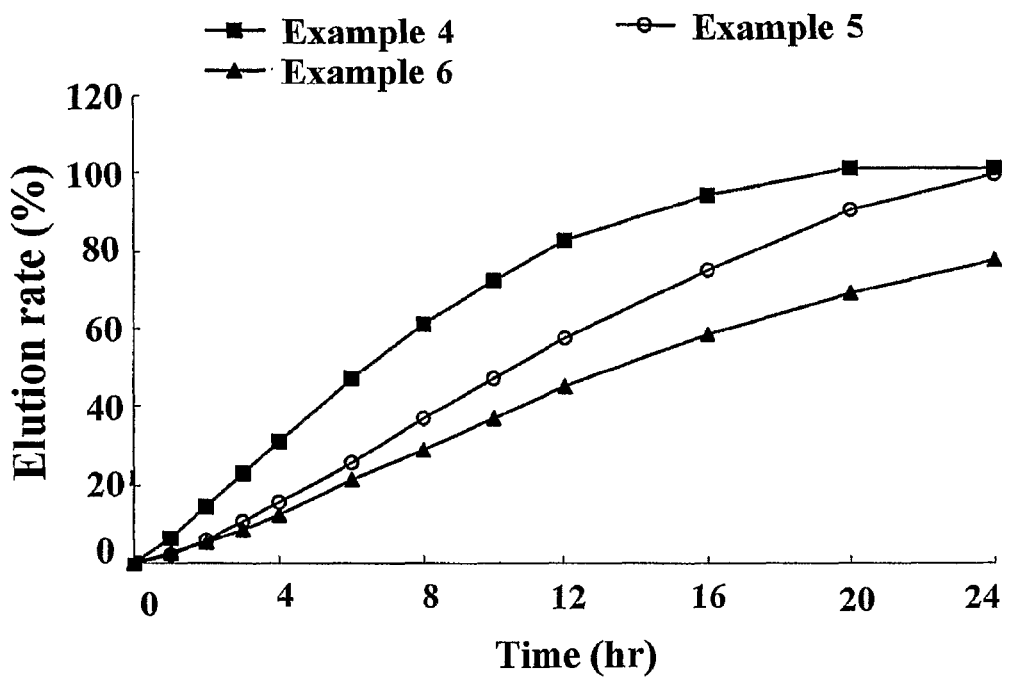
FIG. 3 presents a diagram comparing elution rates of the sustained release formulations prepared in Examples 4 to 6 depending on the amount of xanthan gum.

The result in FIG. 3 showed that the dissolution rate of the drug is inversely proportion to the amount of xanthan gum, which suggests that the xanthan gum functions as a sustained release carrier. Accordingly, it can be inferred that a hydrogel having stronger strength is formed by increasing the amount of xanthan gum.

Test Example 4

Dissolution Test for the Amount of HPMC 2208

The formulations prepared in Examples 7 to 9 were subjected to in vitro dissolution test at 100 rpm according to the same method as described in Test Example 2.

Figure 4:
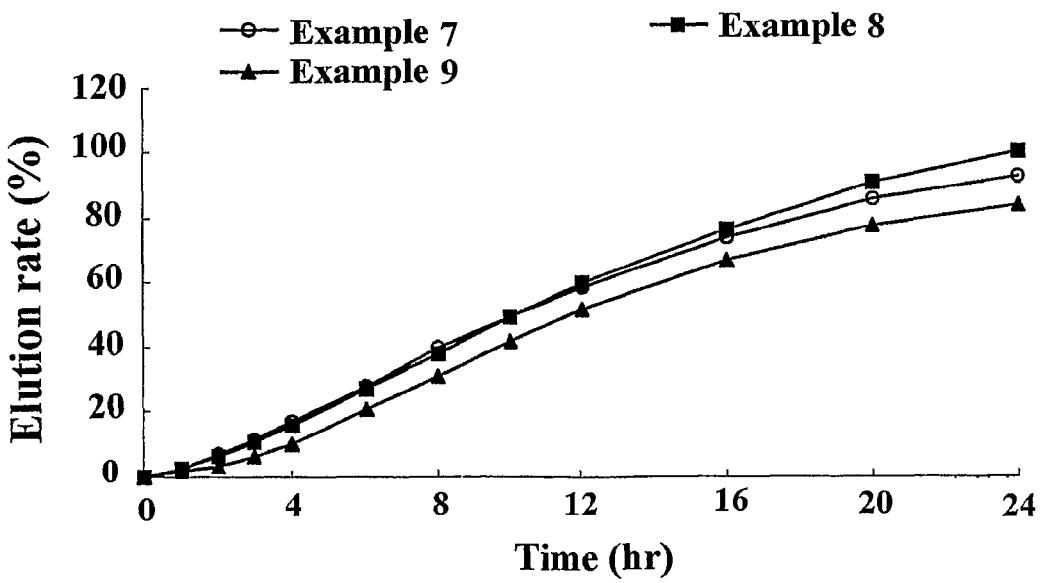
FIG. 4 depicts a diagram comparing elution rates of the sustained release formulations prepared in Examples 7 to 9 depending on the amount of HPMC 2208.

As shown in FIG. 4, it was found that the dissolution rate of the drug is proportional to the amount of HPMC until the amount of HPMC reaches certain concentration, after which it becomes inversely proportional to the amount of HPMC.

These results showe that HPMC functions as a gel hydration accelerator, but it may be capable of acting as a sustained release carrier when added in high concentration.

Test Example 5

Tests for Oral Absorption Rate and Distribution/Excretion Into Bile Juice

In order to compare a bioavailability and a sustained releasing effect of the orally administrable formulation of the present invention and examine its therapeutic effect on the liver as a target site of HMG-CoA reductase inhibitor, tests for bioavailability and distribution/excretion into bile juice when orally administered to rats were conducted as follows. At this time, the sustained release formulation prepared in Example 5 was used as a test sample and -ZOCOR® (simvastatin) (Korea MSD Ltd.) known as a rapid release formulation of simvastatin was used as a control sample.

14 to 15-week old male Sprague Dawley rats (average body weight: 250 g) were divided into two groups, each consisting of 5 rats. The rats were acclimated for more than 4 days allowing free access to food and water. And then, the rats were put on a fast over a period of 48 hrs, while they were allowed to free access to water. Before the administration of each sample, the rats were etherized, had their hands and feet tied, and then, undergone a surgical operation for inserting a tube into an artery and an vein of the femoral region, and a bile duct to take blood and bile juice at the same time, respectively. The loss of body fluid was supplemented by injecting a physiological saline solution through the tube inserted into the vein. After then, each of the test and control samples was filled in a capsule for oral administration to the rats in an amount corresponding to 10 mg/kg of simvastatin, and orally administered to the rats using a proper injection tool, respectively. Blood samples were taken from the tubes inserted into the artery and the vein of the rats before the administration, and at 0.5, 1, 1.5, 3, 5, 7, 9, 12 and 24 hrs after the administration. Bile juice samples were taken from the tube inserted into the bile duct of the rats at 1, 2, 3, 5, 7, 9, 12 and 24 hrs after the administration.

The blood concentration and the distribution pattern in bile juice of simvastatin were analyzed by the following.

To each 100 μλ of bile juice and blood samples, 200 μλ of methanol as an internal standard was added and the mixture was shaken to obtain an extract. The extract was centrifuged at 3,000 rpm for 10 min to obtain a supernatant and the supernatant was filtered through a filter paper having a pore size of 0.22 μm. Then, the filtrate was subjected to LC-MS analysis under the following conditions. The analytical results are shown in FIGS. 5 and 6.

Column: Waters Oasis HLB (2.1×50 mm)
Mobile phase: concentration gradient system of acetonitrile, water and 10 mM $NH_4OAc$ (adjusting pH to 4.5 with formic acid)
Injection volume: 50 μλ
Flow rate: 0.3 mλ/min
Detection: SIR mode m/z: 419.4 (simvastatin), 435.3 (simvastatinic acid)

Figure 5:
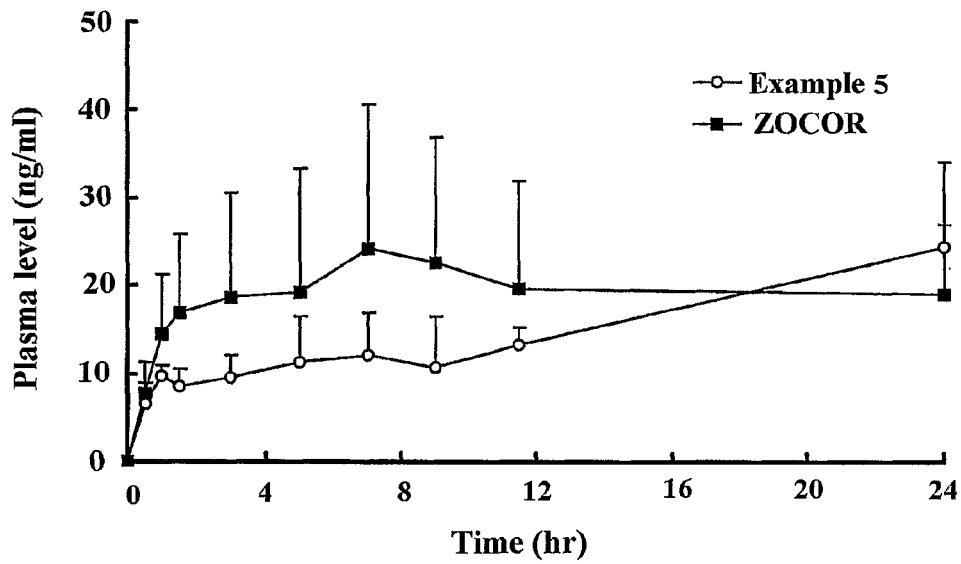
FIG. 5 offers a diagram representing the change in blood simvastatin level after oral administration of the sustained release formulation prepared in Example 5.
Figure 6:
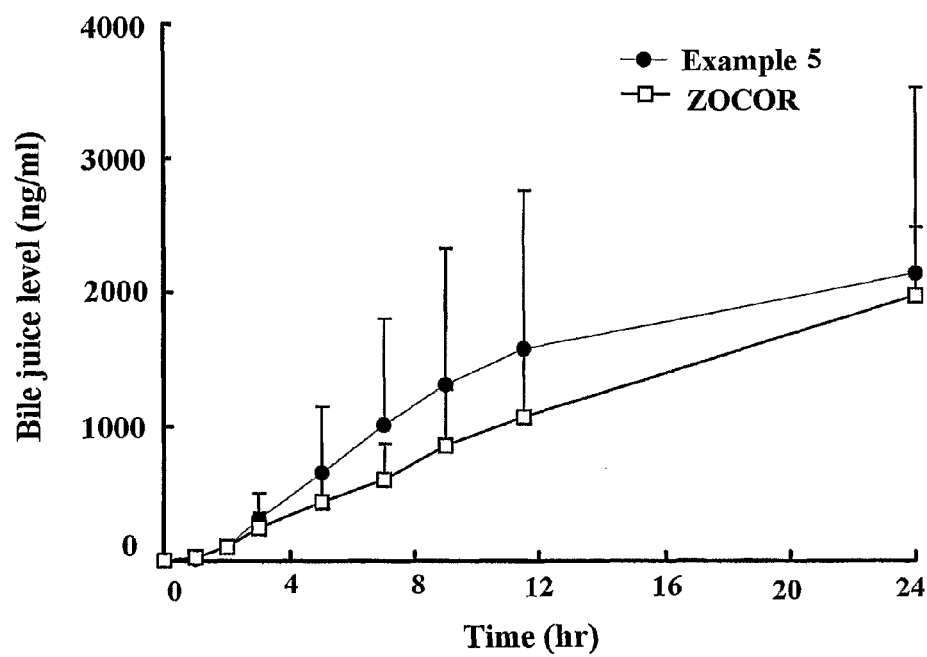
FIG. 6 illustrates a diagram representing distribution and excretion patterns of simvastatin into bile juice after oral administration of the sustained release formulation prepared in Example 5.

As shown in FIG. 5, the sustained release formulation of the present invention showed 79.4 ng/mμ of $C_{max}$ and 249.0 ng·hr/mλ of AUC that were slightly lower than those of the rapid release formulation (88.1 ng/mλ of $C_{max}$ and 266.2 ng·hr/mμ of AUC), but it exerted a desired level of sustained releasing effect. Further, the result in FIG. 6 showed that most of the sustained release formulation of the present invention was found to be present and metabolized in the liver, which was indicative of the fact that the sustained release formulation was more effective for the liver than the rapid release formulation. Considering that the HMG-CoA reductase inhibitor is designed to be effective in the liver wherein more than 95% of them is metabolized, the sustained release formulation of the present invention is the most suitable formulation for oral administration of the HMG-CoA reductase inhibitor.

Test Example 6

Effect of Lowering Cholesterol and Triglyceride Levels

In order to examine a therapeutic effect of the sustained release formulation of HMG-CoA reductase inhibitor on hyperlipidemia caused by a high-cholesterol diet, the sustained release formulation of the present invention was administered to hyperlipidemia induced rats and the changes in the in-blood concentration of cholesterol and triglyceride was measured.

In particular, the preparation of the high-cholesterol diet used for inducing hyperlipidemia and the establishment of a pathologic model were conducted according to the method described by Niiho et al. (Yakugaku Zasshi 110: 604-611, 1991). The high-cholesterol diet was prepared by grinding a common animal feed for a normal diet, passing them through a 40 mesh sieve, and mixing with 5% cholesterol, 0.25% cholic acid and 2.5% olive oil.

Twenty-four 4 to 5-week old male Sprague Dawley rats were used in the following experiments. After weighing the rats and making them uniformly distributed according to their average body weights, they were divided into four groups, each consisting of 6 rats having an average body weight of 202±5 g. The rats were acclimated to the cage environment being set a temperature to 23±2° C. and a relative humidity to 55±15%.

The $1^{st}$ group was a control group which was subjected to the highcholesterol diet during the experiment without treating with a therapeutic drug; and the $2^{nd}$ group was subjected to the high-cholesterol diet with administering -ZOCOR® (simvastatin) once a day in an amount corresponding to 5 mg/kg of simvastatin. The $3^{rd}$ group was subjected to the high-cholesterol diet with administering the sustained release formulation prepared in Example 5 once a day in an amount corresponding to 5 mg/kg of simvastatin; and the 4th group was a normal having no history of receiving the high-cholesterol diet and a therapeutic drug.

Two weeks after the administration, the rats were sacrificed and serum samples were taken from each group. The in-blood concentration of total cholesterol and triglyceride was measured according to a conventional enzyme reaction method, and the results are shown in Tables 5 and 6.

TABLE 5

| Animal group | Total cholesterol* (mg/dl) | Ratio of cholesterol level to a control (%) |
|---|---|---|
| The $1^{st}$ group (control) | 671.5 ± 84.1 | 100 |
| The $2^{nd}$ group (ZOCOR ® (simvastatin)) | 567.9 ± 93.2 | 84.6 |
| The $3^{rd}$ group (the sustained release formulation of Example 5) | 453.0 ± 77.0 | 67.5 |
| The $4^{th}$ group (normal) | 81.0 ± 8.2 | — |

*an average concentration of total cholesterol ± standard deviation

TABLE 6

| Animal group | Triglyceride* (mg/dl) | Ratio of triglyceride level to a control (%) |
|---|---|---|
| The $1^{st}$ group (control) | 242.4 ± 12.6 | 100 |
| The $2^{nd}$ group (ZOCOR ®) (simvastatin)) | 187.0 ± 24.6 | 77.1 |
| The $3^{rd}$ group (the sustained release formulation of Example 5) | 157.0 ± 18.0 | 64.8 |
| The $4^{th}$ group (normal) | 120.3 ± 10.1 | — |

*an average concentration of triglyceride ± standard deviation

As shown in Tables 5 and 6, the in-blood concentration of cholesterol and triglyceride of the $1^{st}$ group increased 8-fold and 2-fold higher than those of the $4^{th}$ group (control), respectively, due to the administration of the high-cholesterol diet for 2 weeks. In the $2^{nd}$ (ZOCOR®) and the $3^{rd}$ (the sustained release formulation of Example 5) groups when were subjected to the high-cholesterol diet and the drug for 2 weeks, their in-blood concentration of total cholesterol and triglyceride were significantly lower than those of the control group. In particular, the sustained release formulation of the present invention showed higher inhibitory effect on increasing the in-blood concentration of total cholesterol and triglyceride than the previous rapid release formulation of simvastatin, which results from the prolonged action of the sustained release formulation in the liver.

While the invention has been described with respect to the above specific embodiments, it should be recognized that various modifications and changes may be made to the invention by those skilled in the art which also fall within the scope of the invention as defined by the appended claims.

What is claimed is:

1. A sustained release formulation for oral administration of an HMG-CoA reductase inhibitor comprising:
   a spray-dried solid dispersant in the form of particles having a particle size ranging from 5 to 200 µm, wherein the solid dispersant contains the HMG-CoA reductase inhibitor, a solubilizing agent, and a stabilizing agent;
   a mixture of sodium alginate and xanthan gum as a sustained release composite carrier; and
   a mixture of propylene glycol ester alginate and hydroxypropyl methyl cellulose as a gel hydration accelerator.

2. The sustained release formulation of claim 1, wherein the amount of the solubilizing agent is 0.05 to 20 weight part; the amount of the stabilizing agent is 0.01 to 0.1 weight part; the amount of the sustained release composite carrier is 3 to 30 weight part; and the amount of the gel hydration accelerator is 0.1 to 5 weight part based on 1 weight part of the HMG-CoA reductase inhibitor.

3. The sustained release formulation of claim 1, wherein the HMG-CoA reductase inhibitor is selected from the group consisting of mevastatin, lovastatin, pravastatin, lactone of pravastatin, velostatin, simvastatin, rivastatin, fluvastatin, atorvastatin, cerivastatin and a pharmaceutically acceptable salt thereof.

4. The sustained release formulation of claim 3, wherein the HMG-CoA reductase inhibitor is simvastatin or a pharmaceutically acceptable salt thereof.

5. The sustained release formulation of claim 1, wherein the solubilizing agent is selected from the group consisting of d-α-tocopheryl polyethylene glycol 1000 succinate, polyoxyethylene stearic acid ester, polyethylene glycol and polyoxypropylene-polyoxypropylene block copolymer.

6. The sustained release formulation of claim 1, wherein the stabilizing agent is selected from the group consisting of butylated hydroxy toluene, butylated hydroxy anisol, erythorbic acid and ascorbic acid.

7. The sustained release formulation of claim 1, wherein the solid dispersant further includes a pharmaceutically acceptable solubilizing carrier.

8. The sustained release formulation of claim 1, wherein the sustained release composite carrier includes 0.1 to 10 weight part of the xanthan gum based on 1 weight part of the sodium alginate.

9. The sustained release formulation of claim 1, wherein the sustained release composite carrier further includes locust bean gum.

10. The sustained release formulation of claim 9, wherein the sustained release composite carrier includes 0.1 to 5 weight part of the locust bean gum based on 1 weight part of the sodium alginate.

11. The sustained release formulation of claim 1, wherein the gel hydration accelerator includes 0.05 to 20 weight part of the propylene glycol ester alginate based on 1 weight part of the hydroxypropyl methyl cellulose.

12. The sustained release formulation of claim 11, wherein the hydroxypropyl methyl cellulose has a viscosity ranging from 4,000 to 100,000 cps.

13. The sustained release formulation of claim 1, further comprising a pharmaceutically acceptable additive selected from the group consisting of a binder, a lubricating agent, a sweetening agent and an excipient.

14. A method for preparing the sustained release formulation of claim 1, comprising the steps of:
   (1) mixing a HMG-CoA reductase inhibitor, a solubilizing agent, and a stabilizing agent in a solvent to obtain a solid dispersant;
   (2) homogeneously mixing the sustained release composite carrier being a mixture of sodium alginate and xanthan gum and the gel hydration accelerator being a mixture of propylene glycol ester alginate and hydroxypropyl methyl cellulose with the solid dispersant to form a first mixture;
   (3) adding a pharmaceutically acceptable additive to the first mixture to form a second mixture; and
   (4) dry-mixing and formulating the second mixture into a solid formulation, wherein, the solid dispersant is prepared by a spray-drying Method and is in the form of particles having a particle size ranging from 5 to 200 µm.

15. A sustained release formulation for oral administration of an HMG-CoA reductase inhibitor comprising:
   a spray-dried solid dispersant in the form of particles having a particle size ranging from 5 to 200 µm, wherein the solid dispersant consists of the HMG-CoA reductase inhibitor, a solubilizing agent, and a stabilizing agent;
   a mixture of sodium alginate and xanthan gum as a sustained release composite carrier; and
   a mixture of propylene glycol ester alginate and hydroxypropyl methyl cellulose as a gel hydration accelerator.

* * * * *